US00PP10252P

United States Patent [19]

VandenBerg

[11] Patent Number: Plant 10,252

[45] Date of Patent: Feb. 24, 1998

[54] CHRYSANTHEMUM PLANT NAMED 'GILROY'

[75] Inventor: Cornelis P. VandenBerg, Salinas, Calif.

[73] Assignee: Yoder Brothers, Inc., Barberton, Ohio

[21] Appl. No.: 771,897

[22] Filed: Dec. 23, 1996

[51] Int. Cl.[6] ..... A01H 5/00

[52] U.S. Cl. ..... Plt./79

[58] Field of Search ..... Plt./78, 79

*Primary Examiner*—Howard J. Locker

*Attorney, Agent, or Firm*—C. A. Whealy

[57] ABSTRACT

A distinct cultivar of Chrysanthemum plant named 'Gilroy', characterized by its upright and uniform plant habit; large decorative disbud-type inflorescences that are 10.2 to 11.7 cm in diameter; attractive medium to light bronze-colored ray florets; and excellent postproduction longevity with inflorescences maintaining good substance and color for about four weeks in an interior environment.

3 Drawing Sheets

The present invention relates to a new and distinct cultivar of Chrysanthemum plant, botanically known as *Dendranthema grandiflora* and referred to by the cultivar name Gilroy.

The new cultivar is a product of a planned breeding program conducted by the inventor in Salinas, Calif. The objective of the breeding program is to create new Chrysanthemum cultivars having inflorescences with desirable inflorescence forms and floret colors and good post-production longevity.

The new cultivar originated from a cross made by the inventor in February, 1993, of the cultivar Charm (disclosed in U.S. Plant Pat. No. 5,502) as the male, or pollen, parent with an unnamed proprietary seedling selection as the female, or seed, parent.

The cultivar Gilroy was discovered and selected by the inventor as a flowering plant within the progeny of the stated cross in a controlled environment in Salinas, Calf., in December, 1993. The selection of this plant was based on its desirable inflorescence form and ray floret color and good post-production longevity.

Asexual reproduction of the new cultivar by terminal cuttings taken in a controlled environment in Salinas, Calif., has shown that the unique features of this new Chrysanthemum are stable and reproduced true to type in successive generations.

The cultivar Gilroy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gilroy'. These characteristics in combination distinguish 'Gilroy' as a new and distinct cultivar:

1. Upright and uniform plant habit.
2. Large decorative disbud-type inflorescences that are 10.2 to 11.7 cm in diameter.
3. Attractive medium to light bronze-colored ray florets.
4. Excellent postproduction longevity with inflorescences maintaining good substance and color for about four weeks in an interior environment.

The new Chrysanthemum is similar in ray floret color to the Chrysanthemum cultivar El Paso (disclosed in U.S. Plant Pat. No. 8,831). However in side-by-side comparisons in Salinas, Calif., under commercial practice, plants of the new Chrysanthemum differed from plants of the cultivar El Paso in the following characteristics:

1. Plants of the new Chrysanthemum are shorter than plants of the cultivar El Paso.

2. Leaves of plants of the new Chrysanthemum have shorter lower leaf lobes than leaves of plants of the cultivar El Paso.
3. Leaves of plants of the new Chrysanthemum have divergent sinuses between lateral lobes whereas plants of the cultivar El Paso have parallel sinuses between lateral leaf lobes.
4. Plants of the new Chrysanthemum flower 2 to 3 days earlier than plants of the cultivar El Paso.
5. Plants of the new Chrysanthemum have slightly larger inflorescences than plants of the cultivar El Paso.
6. Ray florets of plants of the new Chrysanthemum have a shorter corolla tube than ray florets of plants of the cultivar El Paso.

The accompanying photographs illustrate the overall appearance of the new cultivar.

The first sheet is a colored photograph comprising a top perspective view of a typical flowering plant of 'Gilroy'. This photograph shows the colors as true as it is reasonably possible to obtain in colored reproductions of this type. Floret and foliage colors in the photograph may differ from the actual colors due to light reflectance.

The second sheet is a black and white photograph comprising a top perspective view of inflorescences of the cultivar Gilroy showing left to right: adaxial, abaxial and lateral surfaces.

The third sheet is a black and white photograph comprising a top perspective view of the abaxial (top of photo) and adaxial (bottom of photo) surfaces of leaves of the cultivar Gilroy at three different stages of development, left to right: mature, intermediate and immature, showing the differences in size and lobation development.

In the following description, color references are made to The Royal Horticultural Society Colour Chart except where general terms of ordinary dictionary significance are used. The following observations and measurements describe plants grown in Leaminton, Ontario, Canada, under greenhouse conditions which approximate those generally used in commercial potted chrysanthemum production. Four unrooted cuttings were directly stuck in a 15-cm container. Measurements and numerical values represent averages for a minimum of four typical flowering containers.

Botanical classification: *Dendranthema grandiflora* cultivar Gilroy.

Commercial classification: *Decorative disbud-type pot chrysanthemum.*

Parentage:

*Male or pollen parent.*—*Dendranthema grandiflora* cultivar Charm (U.S. Plant Pat. No. 5,502).

*Female or seed parent.*—Unnamed proprietary seedling selection.

Propagation:

*Type.*—Terminal tip cuttings.

*Time to rooting.*—Seven to ten days with soil temperatures of 21C.

*Rooting habit.*—Fine, fibrous and well-branched.

Plant description:

*Appearance.*—Perennial herbaceous decorative disbud-type pot Chrysanthemum. Upright, uniform habit and moderate branching. Four to five lateral branches develop after removal of terminal apex (pinching).

*Plant height.*—18 to 23 cm.

*Foliage description.*—Leaf arrangement: Alternate. Leaf size, fully expanded: Length: About 9 cm. Width: About 5.5 cm. Leaf apex: Mucronate. Leaf base: Attenuate. Leaf margin: Palmately lobed, sinuses between lateral lobes divergent. Leaf texture: Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation adaxial surface: 147B. Venation abaxial surface: 147B.

Inflorescence description:

*Appearance.*—Decorative disbud-type inflorescence form with medium to light bronze ray florets. Inflorescences borne on terminals above foliage, arising from leaf axils. Disk and ray florets arranged acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions flower about 50 to 56 days later.

*Postproduction longevity.*—In an interior environment, inflorescences of cut flowering stems will maintain good color and substance for about four weeks in an interior environment.

*Quantity or Inflorescences.*—As a disbud-type, all flowering stems are removed but one to maximize Inflorescence size.

*Inflorescence size.*—Diameter: 10.2 to 11.7 cm. Depth (height): About 2.5 cm. Diameter of disc: About 5 mm.

*Ray florets.*—Shape: Narrowly oblong, straight, short corolla tube. Size: Length: About 5 cm. Width: About 1.3 cm. Apex: Acute. Margin: Entire. Texture: Ribbed lengthwise, smooth, glabrous. Aspect: Flat. Number of ray florets per inflorescence: About 265. Color: Adaxial surface: 22B/22C. Abaxial surface: 22D.

*Disc florets.—Inconspicuous.*Shape: Tubular. Size: Length: About 6 mm. Width: About 1 mm. Number of disc florets per inflorescence: About 24. Color: Immature: 154A. Mature: Apex: 9A. Base: White, 155D.

*Peduncle.*—Aspect: Strong, erect. Texture: Pubescent. Color: 143A.

*Reproductive organs.*—Androecium: Present on disc florets only. Anther color: 9A. Pollen: Little, 9A in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Gilroy', as illustrated and described.

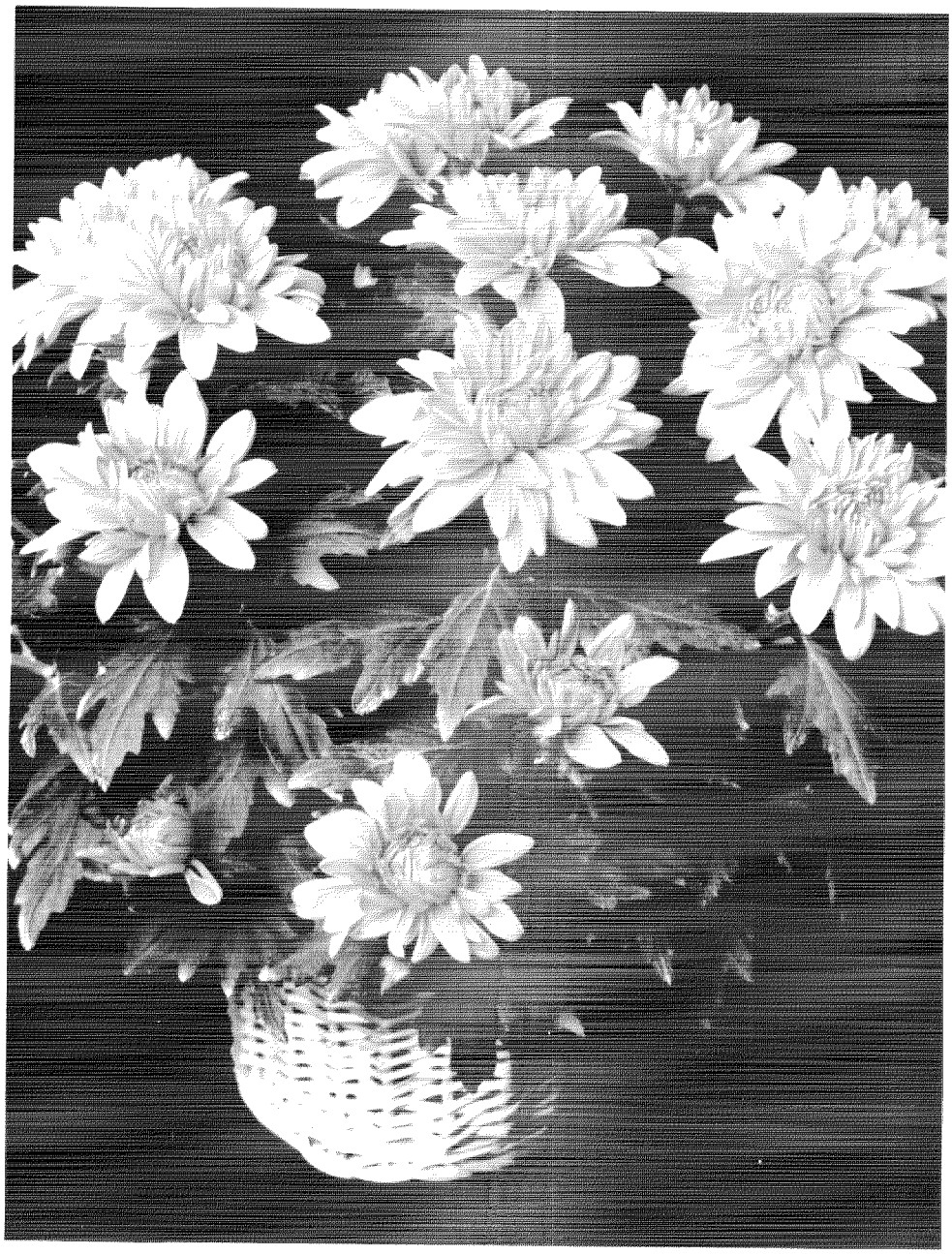

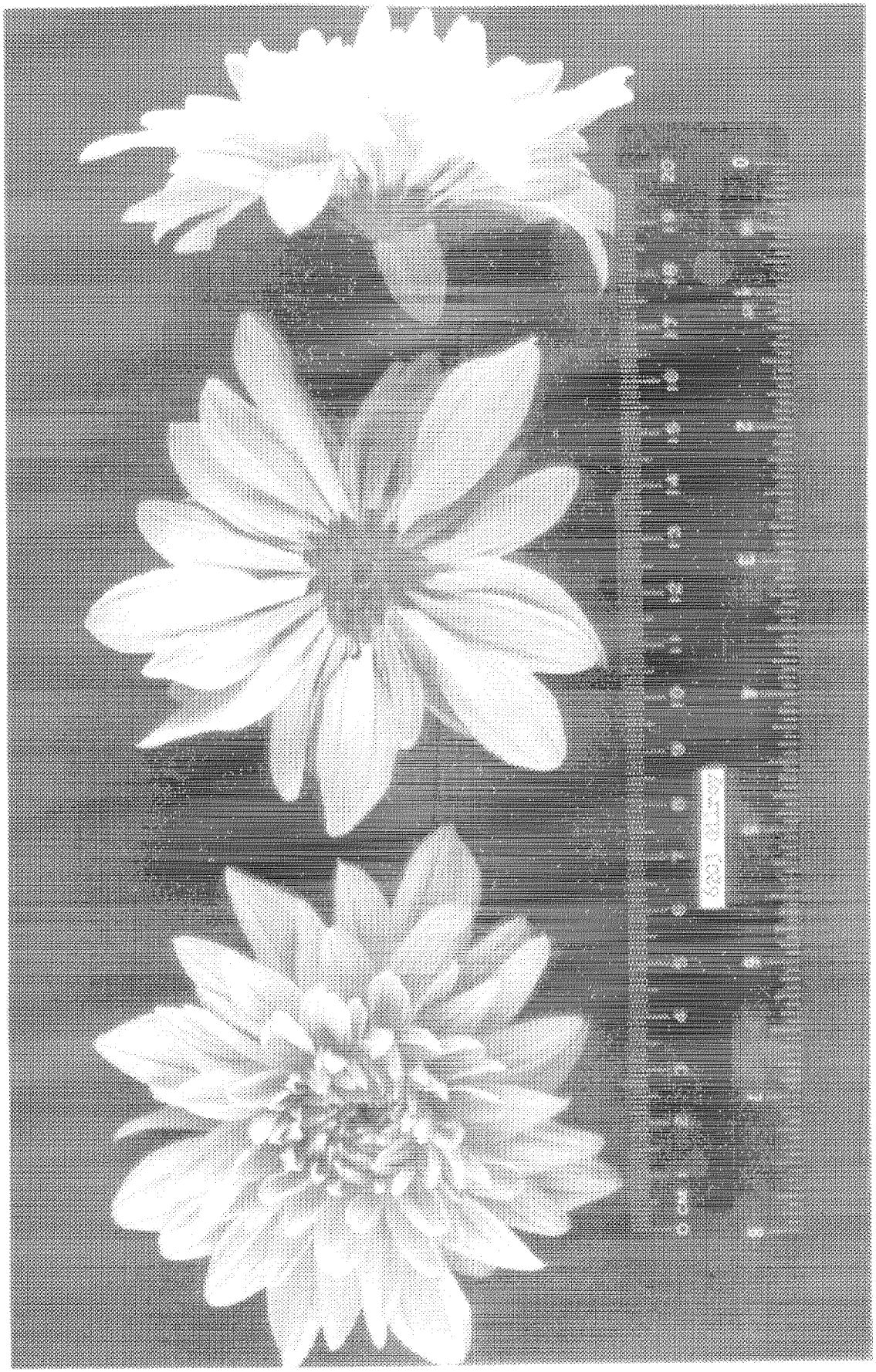

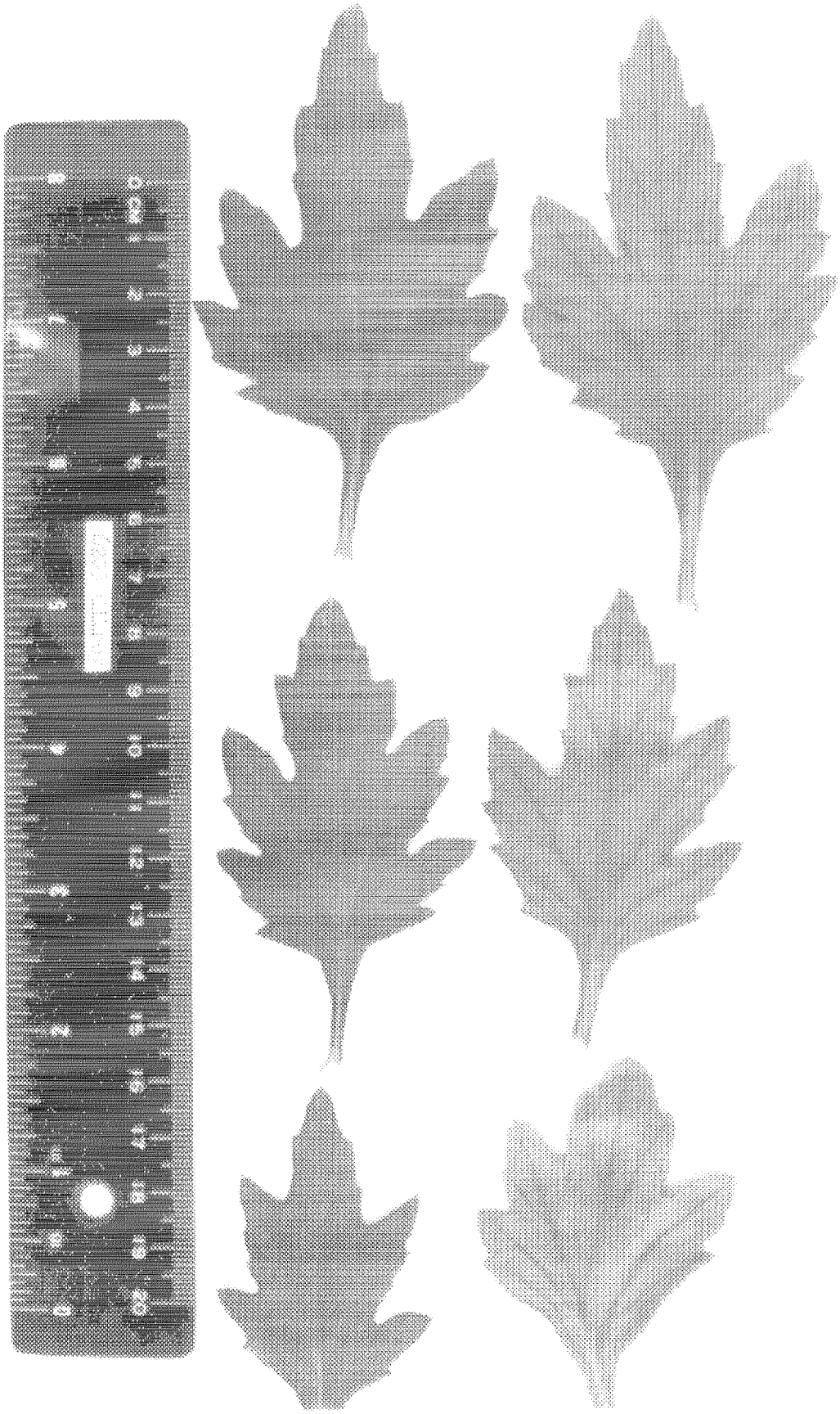

* * * * *